United States Patent [19]

Yamamoto

[11] Patent Number: 4,889,876

[45] Date of Patent: Dec. 26, 1989

[54] COMPOSITE SUBSTANCE AND A METHOD FOR THE PRODUCTION OF THE SAME

[76] Inventor: Tohru Yamamoto, c/o Nakato Laboratory Inc., 6, Ohshinohara, Yasu-cho, Yasu-gun, Shiga-ken, Japan

[21] Appl. No.: 175,554

[22] Filed: Mar. 31, 1988

[30] Foreign Application Priority Data

Apr. 2, 1987 [JP] Japan ................................. 62-082279

[51] Int. Cl.$^4$ .............................................. C08F 2/46
[52] U.S. Cl. .................................... 522/135; 522/144; 522/172; 528/10; 528/12; 528/21; 528/29; 528/25; 528/30; 528/392; 526/279; 501/88; 501/89; 501/98
[58] Field of Search ...................... 522/135, 144, 172; 528/392, 10, 30, 12, 25, 29, 21; 526/279; 501/88, 89, 98

[56] References Cited

U.S. PATENT DOCUMENTS

| | | | |
|---|---|---|---|
| 3,625,934 | 12/1971 | Rinse | 528/30 |
| 4,684,697 | 8/1987 | Chang et al. | 528/10 |
| 4,753,827 | 6/1988 | Yoldas et al | 528/29 |
| 4,754,012 | 6/1988 | Yoldas et al. | 528/29 |

Primary Examiner—Melvyn I. Marquis
Attorney, Agent, or Firm—Irell & Manella

[57] ABSTRACT

A composite substance made of conjugated polymers that contain an inorganic moiety and an organic moiety in their molecule is provided. The conjugated polymers are produced from metal alkoxides and silane coupling agents, or else from metal alkoxides, silane coupling agents, and organic monomers. The conjugated polymers may be fired to give another composite substrate of this invention. These composite substances have both inorganic and organic characteristics, thereby attaining the excellent heat-stability, mechanical strength, resistance to chemicals, and workability.

28 Claims, No Drawings

COMPOSITE SUBSTANCE AND A METHOD FOR THE PRODUCTION OF THE SAME

BACKGROUND OF THE INVENTION

1. Field of the Invention:

This invention relates to a composite substance and to a method for its manufacture; in particular, it relates to composite substance consisting of a conjugated polymer produced from a metal alkoxide, silane coupling agent, and, when necessary, an organic monomer, with high mechanical strength, excellent heat-stability and resistance to chemicals, and superior workability.

2. Description of the Prior Art:

Inorganic compounds (including inorganic polymers) have excellent heat-stability, mechanical strength, and resistance to chemicals. On the other hand, organic polymers are flexible and have excellent workability, and they are soluble in organic solvents. Organic polymers such as aromatic polyamides that have high tensile strength, high elastic coefficients, and excellent heat-resistance have also been developed.

Preparation of a composite has been carried out in which the special characteristics such as these of inorganic compounds or inorganic polymers and these of organic polymers are combined. This kind of a composite can be manufactured by, for example, the following methods: (1) a method in which a powder of an inorganic substance, for example, a metallic powder, is mixed with an organic polymer; (2) a method in which an inorganic fiber is incorporated into an organic polymer; and (3) a method in which glass microballoons are incorporated into an organic polymer. However, because the composites that are obtained by these methods are all essentially simple mixtures that contain an organic polymer and an inorganic substance, the heat-stability and mechanical strength of the composites are not satisfactory. Also, it is difficult to mix the inorganic substances uniformly with the organic polymers, and to achieve a uniform mixture, a complicated procedure is needed. The result is that the composite obtained has a high cost.

In order to solve the difficulties mentioned above, there have been suggested several methods by which the inorganic material is given the characteristics of organic substances. In one method among them, specific elements are chemically bound to the inorganic material for the purpose of improving the characteristics of the inorganic material for example, nitrogen is introduced into a carbon material to give a carbon nitride, said carbon material thereby having improved characteristics. In another method, the binding between the atoms of the inorganic molecules or the arrangement of the inorganic molecules is changed. Also, there is a method in which an organic polymer is reacted with a metallic compound, or a method in which an organic functional group is introduced into the framework of the inorganic polymer. The compounds obtained by such methods include silicone polymer containing boron and inorganic polymer containing nitrogen. However, in such composite substances as these, the inorganic molecules and the organic molecules are not bound on the molecular level. These composite materials comprise either the inorganic polymer or else the organic polymers as a major component, into which functional groups are introduced, or else a part of which is modified. Accordingly, the characteristics of the composite substance that is obtained are almost exactly the same as the properties of the major component (thus, they have the properties of the inorganic polymer or else the properties of the organic polymer). Also, when an organic functional group is introduced into an inorganic polymer, reagents that are uncommon and expensive are used. Furthermore, the reaction is a violent one. For that reason, this kind of method is not suited for practical use.

SUMMARY OF THE INVENTION

The composite substance of this invention and the methods for producing the same, which are provided by this invention, overcome the problems mentioned above of the conventional materials and methods.

The composite substance made of conjugated polymers of this invention that contain an inorganic moiety and an organic moiety in their molecule, said polymers being produced from metal alkoxides and silane coupling agents.

Another composite substance of this invention is obtained by the firing of the conjugated polymers mentioned above.

Another composite substance made of conjugated polymers of this invention that contain an inorganic moiety and an organic moiety in their molecule, said polymers being produced from metal alkoxides, organic monomers, and silane coupling agents.

Still another composite substance of this invention is obtained by the firing of the conjugated polymers mentioned above.

The present invention provides a method for the production of composite substances made of conjugated polymers, comprising the steps of: adding an acid catalyst for sol-gel methods to a solution or a dispersion containing metal alkoxides, silane coupling agents, and water so as to cause the hydrolysis of the metal alkoxides and the silane coupling agents; and adding a base catalyst for sol-gel methods to the reaction mixture so as to cause the polycondensation of the hydrolysate to form said conjugated polymers.

The present invention also provides a method for the production of composite substances consisting of a fired conjugated polymers comprising the further step of firing the conjugated polymers mentioned above.

The present invention also provides a method for the production of composite substances made of conjugated polymers, comprising the steps of: adding an acid catalyst for sol-gel methods to a solution or a dispersion containing metal alkoxides, silane coupling agents, and water so as to cause the hydrolysis of the metal alkoxides and the silane coupling agents; and adding organic monomers to the reaction mixture; and adding a base catalyst for sol-gel methods to said reaction mixture, and immediately thereafter irradiating the reaction mixture with at least one of these two, ultraviolet light and an electron beam, so that the polycondensation of the hydrolysate occurs with the polymerization of said organic monomers and the hydrolysate of said silane coupling agent to form said conjugated polymers.

The present invention also provides a method for the production of composite substances consisting of a fired conjugated polymers comprising the further step of firing the conjugated polymers mentioned above.

In a preferred embodiment, the metal alkoxide is at least one selected from the group consisting of Si$(OC_2H_5)_4$, Al$(O-iso-C_3H_7)_3$, Ti$(O-iso-C_3H_7)_4$, Zr$(O-t-C_4H_9)_4$, Zr$(O-n-C_4H_9)_4$, Ca$(O-C_2H_5)_2$, Fe(OC$_2$H$_5$)$_3$, V(O—iso—C$_3$H$_7$)$_4$, Sn(O—t—C$_4$H$_9$)$_4$, Li(OC$_2$H$_5$), Be(O—C$_2$H$_5$)$_2$, B(OC$_2$H$_5$)$_3$, P(OC$_2$H$_5$)$_3$, and P(OCH$_3$)$_3$.

In a preferred embodiment, the catalyst for sol-gel methods comprises an acid or its anhydride and organic base, said organic base being a tertiary amine that is substantially insoluble in water and soluble in organic solvents.

In a preferred embodiment, the tertiary amine is at least one selected from the group consisting of N,N-dimethylbenzylamine, tributylamine, tri-n-propylamine, tripentylamine, tripropargylamine, N,N,N-trimethylethylenediamine, and tri-n-hexylamine.

Accordingly, the invention disclosed herein makes possible the objective of (1) providing a composite substance in which there are combined the special characteristics of an inorganic compound, especially an inorganic polymer (i.e., inorganic substances that have repeated units covalently bonded), and an organic compound; that is, a composite substance with superior heat-stability, mechanical strength, resistance to chemicals, flexibility, and workability (workability means thermoplasticity, solubility in solvents, mechanical workability, etc.); (2) providing a composite substance that can be used as a special paint (i.e., heat-resistant paint, insulating paint, etc.), dispersing agent for a fiber-reinforced metallic composite or fiber-reinforced ceramic composite, whisker material, material for fibers, agent to improve the heat-resistance of various kinds of polymers or various kinds of adhesives, because of its superior characteristics mentioned above; and (3) providing a method for the manufacture of a composite substance with the superior characteristics mentioned above by a simple procedure.

DESCRIPTION OF THE PREFERRED EMBODIMENTS

This invention was accomplished by the knowledge of the inventor that if an inorganic monomer such as metal alkoxide and a silane coupling agent are hydrolyzed and polycondensed, they will become bound together on the molecular level, so as to give a conjugated polymer having an inorganic moiety and an organic moiety.

Also, this invention was accomplished by the knowledge of the inventor that if an polymerizable organic monomer is added to the reaction system mentioned above to cause a polymerization reaction between said organic monomer and the silane coupling agent at the same time as the polycondensation reaction mentioned above, the metal alkoxide, the silane coupling agent, and the organic monomer will become bound together on the molecular level resulting in a conjugated polymer with an inorganic moiety and an organic moiety.

The metal alkoxides used in the composite substance of this invention can be obtained by adding methanol, ethanol, isopropanol, and other well-known alcohols to metal oxides such as alumina, silica, titanium(IV) oxide, and zirconium(IV) oxide. For example, Si(OC$_2$H$_5$)$_4$, Al(O—iso—C$_3$H$_7$)$_3$, Ti(O—iso—C$_3$H$_7$)$_4$, Zr(O—t—C$_4$H$_9$)$_4$, Zr(O—n—C$_4$H$_9$)$_4$, Ca(OC$_2$H$_5$)$_2$, Fe(OC$_2$H$_5$)$_3$, V(O—iso—C$_3$H$_7$)$_4$, Sn(O—t—C$_4$H$_9$)$_4$, Li(OC$_2$H$_5$), Be(OC$_2$H$_5$)$_3$, B(OC$_2$H$_5$)$_3$, P(OC$_2$H$_5$)$_3$, and P(OCH$_3$)$_3$ can be used.

The silane coupling agent used for the composite substance of this invention can be any of the well-known silane coupling agents, such as (γ-glycidoxypropyl)trimethoxysilane, (γ-glycidoxypropyl)-methyldiethoxysilane, β-(3,4-epoxycyclohexyl)ethyltrimethoxysilane, vinyltrimethoxysilane, vinyltrichlorosilane, vinyltris(β-methoxyethoxy)silane, vinyltriacetoxysilane, (γ-methacryloxypropyl)trimethoxysilane, N-β-(N-vinylbenzylaminoethyl)-γ-aminopropyltrimethoxysilane hydrochloride, γ-aminopropyltriethoxysilane, N-phenyl-γ-aminopropyltrimethoxysilane, γ-(2-aminoethyl)aminopropyltrimethoxysilane, γ-(2-aminoethyl)aminopropylmethyldimethoxysilane, γ-mercaptopropyltrimethoxysilane, γ-mercaptopropylmethyldimethoxysilane, methyltrimethoxysilane, methyltriethoxysilane, hexamethyldisilazane, γ-anilinopropyltrimethoxysilane, γ-chloropropyltrimethoxysilane, γ-chloropropylmethyldimethoxysilane, methyltrichlorosilane, dimethyldichlorosilane, trimethylchlorosilane, octadecyldimethyl-(3-(trimethoxysilyl)propyl)-ammonium chloride, a mixture of aminosilanes, etc. For every 100 parts by weight of the metal alkoxide mentioned above, 1-300 parts by weight of the silane coupling agent can be used, and preferably 10-40 parts by weight. If less than one part by weight is used, the crosslinked areas of the composite substance obtained become small, and the properties of mechanical strength and resistance to heat are inferior to a composite substance with more crosslinked areas. Also, if an organic monomer is not used, the organic moiety of the composite substance obtained becomes small, and the flexibility and workability will not be good. If more than 300 parts by weight of the silane coupling agent is used, the properties of the composite substance are not very different from that obtained with less, and the use is expensive.

As organic monomers, there are acrylic acid, methacrylic acid, dimethylformamide, acrylonitrile, styrene, methyl acrylate, ethyl acrylate, methyl methacrylate, ethyl methacrylate, etc. However, any vinyl-type monomer, not just those listed here, can be used. This kind of organic monomer is used within the limits of 300 parts by weight or less for every 100 parts by weight of the metal alkoxide mentioned above, and preferably 3-300 parts by weight, with still more preferable limits of 10-100 parts by weight. If more than 300 parts by weight is used, the inorganic properties of the composite substance will decline.

The catalyst for sol-gel method (which is used to catalyze hydrolysis and polycondensation reactions for the metal alkoxides and silane coupling agents mentioned above) includes acids, their anhyrides, and organic bases. These organic bases are tertiary amines that are substantially insoluble in water and soluble in organic solvents.

As the acid used as a catalyst, it is possible to use mineral acid such as hydrochloric acid, sulfuric acid, nitric acid, etc. It is possible to obtain the same effects with the use of the anhydride of mineral acids, for example, with hydrogen chloride gas. Also, organic acids and their anhydrides can be used. For example, tartaric acid, phthalic acid, maleic acid, dodecylsuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride can be used. Per mole of the metal alkoxide, 0.01 mol or more of these acids, and preferably 0.01-0.5 mol, can be used. If the amount of the acid is less than 0.01 mol, the hydrolysis of the metal alkoxides does not proceed substantially.

As such tertiary amines used as a catalyst, N,N-dimethylbenzylamine, tributylamine, tri-n-propylamine, tripentylamine, tripropargylamine, N,N,N-trimethylethylenediamine, tri-n-hexylamine, etc., can be used. The tertiary amine can be used at equimolar amounts or in excess amounts of the acid mentioned above; preferably, it is used in amounts ranging from 0.01 to 0.06 mol per mole of the metal alkoxide. The amount of tertiary amine to be used can be chosen within the limits mentioned above with consideration of its degree of dissociation. If there is too little tertiary amine, then after the hydrolysis of the metal alkoxide, the rate of polycondensation is greatly slowed.

As the solvent that can be used in the method, in addition to the water used in the hydrolysis, it is possible to use an organic solvent. As the organic solvent, solvents that are miscible with water or solvents that can be partly dissolved in water can be used. These include, for example, methanol, ethanol, butanol, n-propanol, isopropanol, pentanol, hexanol, acetone, methyl ethyl ketone, and formamide.

The conjugated polymer (i.e., the composite substance of this invention) is prepared by the following two main methods. In the first method, a polymer is prepared from metal alkoxides and silane coupling agents. In the second method, a polymer is prepared from metal alkoxides, silane coupling agents, and organic monomers.

In the first method, for example, the metal alkoxide and silane coupling agent mentioned above are dissolved in the organic solvent mentioned above, such as, for example, alcohol. The concentration of the metal alkoxide is not set within any particular limits, but ordinarily, it is 500–600 g/l. Next, water is added to the metal alkoxide solution. The amount of water that is added is at the proportion of 1–30 moles per mole of the metal alkoxide. The water can be mixed beforehand with the alcohol mentioned above. To this, an acid catalyst (or its anhydride) for the sol-gel methods mentioned above is added and the mixture is stirred at room temperature. With this treatment, hydrolysis is virtually complete. To this mixture, a light-sensitizer, if needed, is added. As the light-sensitizer, diacetyl and the like can be used. The light-sensitizer accelerates the photocondensation reaction brought about by the ultraviolet radiation. Moreover, if needed, other monomers and polymers can be added. As such monomers, there are vinyl-type monomers, and as the polymers, there are copolymers and polymers polymerized from vinyl chloride, vinyl acetate, butadiene, etc. These monomers and polymers are added for the purpose of acceleration of the polymerization and copolymerization reactions described below, and for the purpose of the formation of a homogeneous and strong polymer. The light-sensitizing agent, and other monomers or polymers can be added to the reaction system from the beginning.

Into this reaction mixture, the tertiary amine catalyst (the other of the two forms of the catalyst) is added, and the mixture is irradiated as needed by ultraviolet light and/or by an electron beam. The wavelength of the ultraviolet light is 250 nm or less. If this wavelength is more than 250 nm, the radical polymerization, cross-linking reaction, and polycondensation reaction mentioned below will probably not proceed sufficiently. The dose of radiation with an electron beam can be within the limits of 0.1–50 megarads. The amount of energy is preferably 150–200 kV. If less than 0.1 megarad is used, the radical polymerization, cross-linking reaction, and polycondensation reaction mentioned below will probably not proceed sufficiently. There is no need for more than 50 megarads. The radiation equipment for the electron beam can be, for example, an area beam electronic radiation device such as the Curetron (Nisshin Denki Co.).

By the addition of the tertiary amines mentioned above, the polycondensation reaction of the hydrolyzed metal alkoxide and silane coupling agent is accelerated, and gelation occurs. Moreover, when the silane coupling agent contains, for example, an epoxy moiety, the acid and base catalyst mentioned above cause cleavage of the epoxy ring, and ring-opening polymerization occurs. When a reaction mixture is irradiated with ultraviolet light and/or an electron beam, radicals arise from vinyl groups of the silane coupling agents, and these radicals cause the cross-linking reaction and radical polymerization (i.e., photopolymerization or electron-beam polymerization) of the organic portion of the silane coupling agent. When ultraviolet light is used for radiation, the radicals arise from the light-sensitizer. In addition to an electron beam and ultraviolet light, other kinds of radiation can be used. A general method, in which radical polymerization is carried out by the use of an initiator, with heat, can also be employed.

In these ways, the hydrolysis and polycondensation of the metal alkoxide and the inorganic portion of the silane coupling agent are made to proceed rapidly. Radical polymerization (including cross-linking polymerization) of the organic portion of the silane coupling agent can also be made to proceed rapidly. The reactions mentioned above occur between the silane coupling agents, between the metal alkoxides, and/or between the silane coupling agent and the metal alkoxide. The inorganic portion of the silane coupling agent (i.e., the silica portion) is taken into the framework of inorganic polymer molecules produced from the hydrolysate of the metal alkoxide, or forms an inorganic polymer by polycondensation arising among the silane coupling agents. The organic portion of the silane coupling agent that is attached to the silicon atom forms a cross-linked moiety with an organic portion of the other silane coupling agent molecule.

The polymer formed in this way comprises linear molecules formed by the polycondensation reaction mentioned above, fine particles with a three-dimensional structure being formed by a crosslinking reaction of the said linear molecules, and/or a continuous three-dimensional matrix formed by the gathering of a number of the said polymer particles and the continuation of further polycondensation and crosslinking reactions. These polymers have an inorganic polymer portion formed by the hydrolysis and polycondensation of the metal alkoxide and silane coupling agent and also an organic portion formed by an organic moiety of the silane coupling agent. This organic portion can be an organic polymer formed by polymerization. In other words, the metal alkoxide and the silane coupling agent react to form a polymer in which the metal alkoxide and the silane coupling agent are bound on the molecular level (this can be thought of as a conjugated polymer having an inorganic portion as its major portion and an organic portion as its minor portion).

In the second method, in addition to the metal alkoxide and silane coupling agent used in the first method mentioned above, an organic monomer is used. The organic monomer is added after the acid catalyst is added and hydrolysis has occurred in the first method mentioned above. Then, as a tertiary amine is being added, ultraviolet light and/or an electron beam used for irradiation, which gives rise to radicals from, for example, the vinyl groups of the organic monomer or the silane coupling agent, and these radicals initiate radical polymerization of the organic monomer and of the organic portion of the silane coupling agent. This polymerization reaction occurs between molecules of the organic monomer, and then between molecules of said organic monomer and the organic portions (i.e., epoxy groups, vinyl groups, etc.) of the silane coupling agent. Also, polymerization occurs between the organic portions of the silane coupling agent. These radicals arise from the light-sensitizing agent when ultraviolet light is used for irradiation. As in the first method mentioned above, as well as an electron beam and/or ultraviolet light, other kinds of radiation can be used. A general method in which polymerization is carried out by the use of an initiator, with heat, can also be used.

In the procedures, of the second method mentioned above, the hydrolysis and the polycondensation of the metal alkoxide and the inorganic portion of the silane coupling agent occur, and radical polymerization (including the crosslinking reaction) also proceeds. The reactions mentioned above occur between the metal alkoxides, between the silane coupling agents, between the organic monomers, and/or between two or among three of these components. The inorganic portion of the silane coupling agent (i.e., the silica portion) is taken into the framework of inorganic polymer molecules produced from the hydrolysate of the metal alkoxide, or forms an inorganic polymer by polycondensation arising among the silane coupling agents. The organic portion of the silane coupling agent that is attached to the silicon atom may form a cross-linked moiety with an organic portion of the other silane coupling agent molecule or the organic monomer molecule.

The structure of the polymer formed by the second method is almost the same as in the first method mentioned above. But generally, the polymer has a more complicated crosslinked structure. This polymer has an inorganic polymer portion formed by the hydrolysis and polycondensation of a metal alkoxide and silane coupling agent and an organic portion derived from the organic monomer and the organic groups of the silane coupling agent. This organic portion can be an organic polymer formed by polymerization. In other words, the polymer obtained is a conjugated polymer, in which the metal alkoxide or its polymer and the organic monomer or its polymer are bound at the molecular level via the silane coupling agent.

To form this kind of conjugated polymer, a catalyst for sol-gel methods is of importance. As catalysts, for sol-gel methods, mineral acids are generally known, and their use in the hydrolysis and polycondensation of metal alkoxide in the manufacture of glass is also known. However, if this kind of catalyst is used, the hydrolysis and polycondensation of the metal alkoxide and the silane coupling agent are extremely slow, taking days or weeks. Especially, when the catalyst is used in the second method, the hydrolysis and polycondensation reactions of the metal alkoxide and silane coupling agent are extremely slow, compared to the polymerization of organic monomers. As a result, a homogeneous conjugated polymer is not formed. On the contrary, in this invention, because catalysts (i.e., acids and tertiary amines) for the sol-gel methods mentioned above that has been developed by the inventor are used, the hydrolysis and/or polycondensation reactions of the metal alkoxides and the silane coupling agents are very much accelerated. Therefore, a homogeneous conjugated polymer is formed. The reactions mentioned above are accelerated by the tertiary amine. The tertiary amine is substantially insoluble in water and soluble in organic solvents. Prior to the addition of the tertiary amine the reaction mixture is a homogeneous solution in which the metal alkoxide and silane coupling agent, and/or hydrolysates thereof are dissolved in organic solvent and water. When added to the homogeneous reaction mixture, the tertiary amine can be dispersed uniformly throughout the reaction mixture to form an organic phase. Thus, there is provided an interface of the organic phase and the water phase in the reaction mixture, at which the tertiary amine serves as a catalyst to promote an interfacial polycondensation reaction in situ. Accordingly, the polycondensation reaction proceeds uniformly and rapidly throughout the reaction mixture, resulting in a homogeneous polymer.

By the formation of this conjugated polymer, the reaction system is generally gelated. The time taken for gelation or degree of gelation depends on the amount of water used and the amount of catalyst for the sol-gel method that is used. In general, it is possible to control the time of gelation from about 2 seconds to several dozens of minutes. The reaction system may become a sol or a viscous liquid by changing of the reaction conditions such as the catalyst, etc. The said gelation time is measured from the time when the addition of the tertiary amine causes neutralization of the acid, which brings the pH of the reaction mixture to 7.

In the method of this invention, the polycondensation reaction (including the crosslinking reaction) by the catalyst for the sol-gel methods mentioned above and the radical polymerization reaction brought about by ultraviolet light or an electron beam proceed at low temperatures such as 20°–30° C., so that a conjugated polymer is obtained easily. The conjugated polymer obtained includes an inorganic moiety and an organic moiety in the molecule as above, and generally, it has a crosslinked structure. For that reason, it is very strong, with excellent heat-resistance, high flexibility, and superior workability. That is, the advantages of an inorganic polymer and an organic polymer are combined in it.

The gel, sol, or viscous solution formed in the above reaction can be used in a paint with heat-resistance. This kind of paint adheres to the substrates on which it is to be painted. Whiskers can be prepared from a polymer that is obtained by removing solvent from the reaction mixture.

The composite substance (i.e., the conjugated polymer) obtained in this way can be fired, causing the organic portion to denature because of decomposition, which gives a composite substance with strongly inorganic properties. The firing temperature is preferably within the limits of 300°–1300° C. The fired conjugated polymer obtained is, compared to before being fired, very much stronger, harder, and more resistant to chemicals. Also, the degree of adhesiveness to the base material when the fired conjugated polymer is to be used as a paint is almost unchanged from before the firing. It is considered that these characteristics of fired conjugated polymer are due to the presence of moieties originating in the organic moieties in the molecule. In this regard, the fired conjugated polymer is unlike the inorganic polymer made from metal alkoxide alone.

This kind of composite substance of this invention that is an unfired or fired conjugated polymer has some properties that are characteristic of inorganic compounds and other properties that are characteristic of organic ones. Ways to use this composite substance include the following: special paint with heat-resistance or resistance to chemicals, a dispersing agent for fiber-reinforced metallic composites or fiber-reinforced ceramic composites, a whisker material, a fiber material that has a tensile strength and a flexibility ratio comparable to that of aromatic polyamide fiber, a material to improve heat-resistance in various kinds of polymers, and a material to improve heat-resistance in various kinds of adhesives (e.g., polyimide adhesives, epoxy adhesives, etc.). The heat resistance of this kind of unfired composite substance is 350° C. or more, and the tensile strength is 100 kg/mm$^2$ or more, with an elongation percentage of 400% or more. The heat resistance of this composite substance when fired is about 1350° C., the flexibility ratio is 1.2 ton/mm$^2$ or more, and the tensile strength is about 200 kg/mm$^2$ or more. The manufacture of the conjugated polymer of this invention involves the addition of a compound containing chalcogens, nitrogen, etc., to the solution of the metal alkoxide, which addition confers electrical conductivity or light conductivity to the composite substance that is obtained.

EXAMPLE 1

| Components | Amounts | (molar ratio) |
|---|---|---|
| Ethyl silicate | 25 g | (1) |
| Ethanol | 25 g | |
| Water | 2.16 g | (1) |
| Hydrochloric acid | 0.129 g$^a$ | (0.03) |
| (γ-Glycidoxypropyl) trimethoxysilane (Tore silicone SH6040) | 10 g | |
| N,N—Dimethylbenzylamine | 0.96 g | (0.06) |

NOTE
$^a$Calculated in terms of hydrogen chloride.

After ethanol, ethyl silicate, hydrochloric acid, and water were mixed, (γ-glycidoxypropyl)trimethoxy silane (i.e., silane coupling agent) was added and the mixture was stirred. To the mixture, N,N-dimethylbenzylamine was added, and at the same time, an areabeam electronic radiation device (Cure-tron; Nisshin Denki Co.) was used to irradiate the mixture with an electron beam of 40 megarads for 0.9 seconds. At the time of the irradiation, the temperature of the mixture was 25° C. The viscous liquid obtained was spun to give a thread. The tensile strength of this thread was 100 kg/mm$^2$ or more; the elongation percentage was 400% or more; and the resistance to heat was to 800° C. or more.

EXAMPLE 2

A thread made of the composite substance obtained in Example 1 was fired at 1000° C. for 1 hour. This was spun as in Example 1. The tensile strength of this thread was 200 kg/mm$^2$, the modulus of elasticity was 1.2 ton/mm$^2$, and the resistance to heat was to 800° C. or more.

EXAMPLE 3

| Components | Amounts | (molar ratio) |
|---|---|---|
| Ethyl silicate | 25 g | |
| Titanium tetraisopropoxide | 2.5 g | (1) |
| Aluminium triisopropoxide | 0.8 g | |
| Ethanol | 61 g | |
| (γ-Glycidoxypropyl) trimethoxysilane (Tore silicone SH6040) | 6 g | |
| Water | 23.75 g | (11) |
| Hydrochloric acid | 0.9 g$^a$ | (0.2) |
| N,N—Dimethylbenzylamine | 0.324 g | (0.02) |

NOTE
$^a$Calculated in terms of hydrogen chloride.

Metal alkoxides (i.e., ethyl silicate, titanium tetraisopropoxide, and aluminium triisopropoxide), ethanol, γ-(glycidoxypropyl)trimethoxysilane, and water were mixed, and hydrochloric acid was added to the mixture; then N,N-dimethylbenzylamine was added, and irradiation was carried out with an electron beam of 30 megarads for 0.4 second. The sol obtained was painted on the surfaces of various kinds of substrates so that its thickness would be 20 μm after drying. As substrates, stainless steel plates (SAS 304 and SAS 430), mild steel plates, and plastic plates (polymethylmethacrylate, or PMMA) were used. The painted substrates were dried at 150° C. for 15 minutes in an incubation vat, except for the plastic plate, which was dried at room temperature. The coated substrates obtained were tested by JIS K 5400 (i.e., general testing methods for paints) for the items listed below in Table 1, and the results obtained are shown there.

TABLE 1

| | SAS 304 and SAS 430 | Plastic substrate | Mild steel substrate |
|---|---|---|---|
| Heat-resistance (° C.) | more than 800 | — | 400~500 |
| Impact-resistance | 500 g:50 cm | 500 g:50 cm | 500 g:50 cm |
| Adhesiveness | 100/100 | 100/100 | 100/100 |
| Hardness (lead pencil scale) | more than 6H | more than 6H | more than 6H |
| Resistance to acid (to 5% H$_2$SO$_4$; 24 hr) | 100% | 100% | 100% |
| Resistance to alkali (to 5% NaCH; 24 hr) | 100% | 100% | 100% |
| Water-resistance (boiling water; 2 hr) | 100% | 100% | 100% |
| Resistance to NaCl soln. (spray; 100 hr) | not changed | not changed | not changed |

EXAMPLE 4

The procedure of Example 3 was repeated, except that the molar ratio of water to the metal alkoxide was 10. The results obtained were similar to those in Example 3.

EXAMPLE 5

The procedure of Example 3 was repeated, except that the molar ratio of water to the metal alkoxide was 8. The results obtained were similar to those in Example 3.

EXAMPLE 6

Conditions were the same as in Example 3, except that 2.5 g of zirconium t-butoxide was added as the metal alkoxide. The sol obtained was applied to the surface of electric wire made of copper (the diameter of which was 2 mm) so that the thickness was 20 μm when dried. This was heated and dried. The heat expansion coefficient of the copper used for electric wire was extremely large, but even when the applied material was heated at 300°–400° C., the adhesiveness of the applied layer to the base material (i.e., the electric wire) was good, and there were no cracks or the like.

EXAMPLE 7

| Components | Amounts | (molar ratio) |
|---|---|---|
| Ethyl silicate | 25 g | (1) |
| Ethanol | 25 g | |
| Water | 3.89 g | (1.8) |
| Hydrochloric acid | 0.129 g[a] | (0.03) |
| (γ-Glycidoxypropyl)trimethoxysilane (Tore silicone SH6040) | 10 g | |
| Acrylic acid | 0.86 g | (0.1) |
| N,N—Dimethylbenzylamine | 0.96 g | (0.06) |

NOTE
[a]Calculated in terms of hydrogen chloride.

To a mixture of ethanol, ethyl silicate, water, and γ-(glycidoxypropyl) trimethyoxysilane (i.e., silane coupling agent), hydrochloric acid was added and the mixture was stirred. To this mixture, acrylic acid was added and mixed, and then, while N,N-dimethylbenzylamine was being added, an areabeam electronic radiation device (Curetron, Nisshin Denki Co.) was used to irradiate the mixture with an electron beam of 40 megarads for 0.9 seconds. The temperature of the mixture at the time of irradiation was 25° C. The viscous liquid obtained was spun into a thread. The tensile strength of this thread was 100 kg/mm² or more, the elongation percentage was 400% or more, and the resistance to heat was up to 500° C. or more.

EXAMPLE 8

A fiber made of the composite substance obtained in Example 7 was fired at 1000° C. for 1 hour. The tensile strength of this thread was 200 kg/mm², the modulus of elasticity was 1.2 ton/mm², and the resistance to heat was to 1350° C. or more.

EXAMPLE 9

The procedure of Example 3 was repeated, except that 1.42 g of acrilonitrile (molar ratio 0.2) was added at the same time as the N,N-dimethylbenzylamine. Coated stainless steel plates and coated mild steel plates were dried at 150° C. and heated at 300° C. for 3 minutes. These coated plates obtained were tested by JIS K 5400 (i.e., general testing methods for paints) for the items listed in Table 1, and the results obtained were similar to those in Example 3.

EXAMPLE 10

The procedure of Example 9 was repeated, except that the molar ratio of water to the metal alkoxides was 10. The results obtained were similar to those in Example 9.

EXAMPLE 11

The procedure of Example 9 was repeated, except that the molar ratio of water to the metal alkoxides was 8. The results obtained were similar to those in Example 9.

EXAMPLE 12

| Components | Amounts | (molar ratio) |
|---|---|---|
| Ethyl silicate | 25 g | |
| Titanium tetraisopropoxide | 2.5 g | |
| Aluminium triisopropoxide | 0.1 g | (1) |
| Zirconium tetra-n-butoxide | 2 g | |
| Ethanol | 60 g | |
| (γ-Glycidoxypropyl)trimethoxysilane (Tore silicone SH6040) | 20.8 g | (0.8) |
| Water | 21.6 g | (10.9) |
| Hydrochloric acid | 0.44 g[a] | (0.1) |
| Acrylic acid | 1.48 g | (0.19) |
| N,N—Dimethylbenzylamine | 0.32 g | (0.02) |

NOTE
[a]Calculated in terms of hydrogen chloride.

Using the components listed above, coated electric wire was obtained by a method similar to that of Example 6. When the coated wire was heated at 300°–400° C., the adhesiveness of the applied layer to the substrate (i.e., the electric wire) was good, and there were no cracks or the like.

What is claimed is:

1. A composite substance comprising a conjugated polymer having a major inorganic portion and a minor organic portion, wherein said inorganic portion is an alkoxide compound selected from the group consisting of $Si(OC_2H_5)_4$, $B(OC_2H_5)_3$, $P(OC_2H_5)_3$, $P(OCH_3)_3$, Al(O—iso—$C_3H_7$)$_3$, Ti(O—iso—$C_3H_7$)$_4$, Zr(O—t—$C_4H_9$)$_4$, Zr(O—n—$C_4H_9$)$_4$, $Ca(OC_2H_5)_2$, Fe(OC_2H_5)_3, V(O—iso—$C_3H_7$)$_4$, Sn(O—t—$C_4H_9$)$_4$, $Li(OC_2H_5)$, and $Be(OC_2H_5)_3$, and said organic portion comprises a silane coupling agent selected from the group consisting of (gamma-glycidoxypropyl)trimethoxysilane, (gamma-glycidoxypropyl)methyldiethoxysilane, beta-(3,4-epoxycyclohexyl)ethyltrimethoxysilane, vinyltrimethoxysilane, vinyltrichlorosilane, vinyltris(-beta-methoxyethoxy)silane, vinyltriacetoxysilane, (gamma-methacryloxypropyl)trimethoxysilane, N-beta-(N-vinylbenzylaminoethyl)-gamma-aminopropyltrimethoxysilane hydrochloride, gamma-aminopropyltriethoxysilane, N-phenyl-gamma-aminopropyltrimethoxysilane, gamma-(2-aminoethyl)aminopropyltrimethoxysilane, gamma-(2-aminoethyl)aminopropylmethyldimethoxysilane, gamma-mercaptopropyltrimethoxysilane, gamma-mercaptopropylmethyldimethoxysilane, methyltrimethoxysilane, methyltriethoxysilane, hexamethyldisilazane, gamma-anilinopropyltrimethoxysilane, gamma-chloropropylmethyldimethoxysilane, methyltrichlorosilane, dimethyldichlorosilane, trimethylchlorosilane, and octadecyldimethyl-(3-(trimethoxysilyl)-propyl)ammonium chloride, and an organic monomer selected from the group consisting of acrylic acid, methacrylic acid, dimethylformamide, acrylonitrile, styrene, methyl acrylate, ethyl acrylate, methyl methacrylate, and ethyl methacrylate, wherein said major inorganic portion and said minor organic portion are bound together on a molecular level.

2. A composite substance that is obtained by firing a conjugated polymer having a major inorganic portion and a minor organic portion, wherein said inorganic portion is an alkoxide compound selected from the group consisting of $Si(OC_2H_5)_4$, $B(OC_2H_5)_3$, $P(OC_2H_5)_3$, $P(OCH_3)_3$, $Al(O\text{—iso—}C_3H_7)_3$, $Ti(O\text{—iso—}C_3H_7)_4$, $Zr(O\text{—}t\text{—}C_4H_9)_4$, $Zr(O\text{—}n\text{—}C_4H_9)_4$, $Ca(OC_2H_5)_2$, $Fe(OC_2H_5)_3$, $V(O\text{—iso—}C_3H_7)_4$, $Sn(O\text{—}t\text{—}C_4H_9)_4$, $Li(OC_2H_5)$, and $Be(OC_2H_5)_3$, and said organic portion is a silane coupling agent selected from the group consisting of (gamma-glycidoxypropyl)trimethoxysilane, (gamma-glycidoxypropyl)methyldiethoxysilane, beta-(3,4-epoxycyclohexyl)ethyltrimethoxysilane, vinyltrimethoxysilane, vinyltrichlorosilane, vinyltris(beta-methoxyethoxy)silane, vinyltriacetoxysilane, (gamma-methacryloxypropyl)trimethoxysilane, N-beta-(N-vinylbenzylaminoethyl)-gamma-aminopropyltrimethoxysilane hydrochloride, gamma-aminopropyltriethoxysilane, N-phenyl-gamma-aminopropyltrimethoxysilane, gamma-(2-aminoethyl)-aminopropyltrimethoxysilane, gamma-(2-aminoethyl)amino-propylmethyldimethoxysilane, gamma-mercaptopropyltrimethoxysilane, gamma-mercaptopropylmethyldimethoxysilane, methyltrimethoxysilane, methyltriethoxysilane, hexamethyldisilazane, gamma-anilinopropyltrimethoxysilane, gamma-chloropropylmethyldimethoxysilane, methyltrichlorosilane, dimethyldichlorosilane, trimethylchlorosilane, and octadecyldimethyl-(3-(trimethoxysilyl)propyl)ammonium chloride, wherein said major inorganic portion and said minor organic portion are bound together on a molecular level, said firing temperature being in the range of 300° C. to 1300° C.

3. A composite substance that is obtained by firing a conjugated polymer of claim 1 the firing temperature being in the range of 300° C. to 1300° C.

4. A method for the production of a conjugated polymer, comprising the steps of:

adding an acid catalyst to a mixture containing a silane coupling agent selected from the group consisting of (gamma-glycidoxypropyl)trimethoxysilane, (gamma-glycidoxypropyl)-methyldiethoxysilane, beta-(3,4-epoxycyclohexyl)ethyltrimethoxysilane, vinyltrimethoxysilane, vinyltrichlorosilane, vinyltris(beta-methoxyethoxy)silane, vinyltriacetoxysilane, (gamma-methacryloxypropyl)trimethoxysilane, N-beta-(N-vinylbenzylaminoethyl)-gamma-aminopropyltrimethoxysilane hydrochloride, gamma-aminopropyltriethoxysilane, N-phenyl-gamma-aminopropyltrimethoxysilane, gamma-(2-aminoethyl)aminopropyltrimethoxysilane, gamma-(2-aminoethyl)aminopropylmethyldimethoxysilane, gamma-mercaptopropyltrimethoxysilane, gamma-mercaptopropylmethyldimethoxysilane, methyltrimethoxysilane, methyltriethoxysilane, hexamethyldisilazane, gamma-anilinopropyltrimethoxysilane, gamma-chloropropylmethyldimethoxysilane, methyltrichlorosilane, dimethyldichlorosilane, trimethylchlorosilane, and octadecyldimethyl-(3-(trimethoxysilyl)-propyl)ammonium chloride, water and an alkoxide compound selected from the group consisting of $Si(OC_2H_5)_4$, $B(OC_2H_5)_3$, $P(OC_2H_5)_3$, $P(OCH_3)_3$, $Al(O\text{—iso—}C_3H_7)_3$, $Ti(O\text{—iso—}C_3H_7)_4$, $Zr(O\text{—}t\text{—}C_4H_9)_4$, $Zr(O\text{—}n\text{—}C_4H_9)_4$, $Ca(OC_2H_5)_2$, $Fe(OC_2H_5)_3$, $V(O\text{—iso—}C_3H_7)_4$, $Sn(O\text{—}t\text{—}C_4H_9)_4$, $Li(OC_2H_5)$, and $Be(OC_2H_5)_3$, so as to cause the hydrolysises of said alkoxide compound, and the silane coupling agent, said acid catalyst being selected from the group consisting of hydrochloric acid, sulfuric acid, nitric acid, tartaric acid, phthalic acid, maleic acid, dodecylsuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride, adding a base catalyst to the reaction mixture and irradiating the reaction mixture with ultraviolet light or an electron beam after the addition of said base catalyst thereto, so as to cause the polycondensation of the hydrolysis product of said alkoxide compound, and the hydrolysis product of the silane coupling agent, to form said conjugated polymer, said base catalyst being a tertiary amine that is substantially insoluble in water and soluble in organic solvents.

5. A method according to claim 4, wherein said tertiary amine is at least one selected from the group consisting of N,N-dimethylbenzylamine, tributylamine, tri-n-propylamine, tripentylamine, tripropargylamine, N,N,N-trimethylethylenediamine, and tri-n-hexylamine.

6. A method according to claim 4, wherein said silane coupling agent is added in the proportion of 1 to 300 parts by weight for every 100 parts by weight of said alkoxide compound.

7. A method according to claim 4, wherein said acid and base catalysts are added in amounts of 0.01 mol or more for every mole of said alkoxide compound, respectively.

8. A method according to claim 4, wherein water for the hydrolysis is added in the proportion of 1 to 30 mol for every mole of said alkoxide compound.

9. A method for the production of a composite substance comprising a conjugated polymer, comprising the steps of:

adding an acid catalyst to a mixture containing a silane coupling agent selected from the group consisting of (gamma-glycidoxypropyl)trimethoxysilane, (gamma-glycidoxypropyl)-methyldiethoxysilane, beta-(3,4-epoxycyclohexyl)ethyltrimethoxysilane, vinyltrimethoxysilane, vinyltrichlorosilane, vinyltris(beta-methoxyethoxy)silane, vinyltriacetoxysilane, (gamma-methacryloxypropyl)trimethoxysilane, N-beta-(N-vinylbenzylaminoethyl)-gamma-aminopropyltrimethoxysilane hydrochloride, gamma-aminopropyltriethoxysilane, N-phenyl-gamma-aminopropyltrimethoxysilane, gamma-(2-aminoethyl)aminopropyltrimethoxysilane, gamma-(2-aminoethyl)aminopropylmethyldimethoxysilane, gamma-mercaptopropyltrimethoxysilane, gamma-mercaptopropylmethyldimethoxysilane, methyltrimethoxysilane, methyltriethoxysilane, hexamethyldisilazane, gamma-anilinopropyltrimethoxysilane, gamma-chloropropylmethyldimethoxysilane, methyltrichlorosilane, dimethyldichlorosilane, trimethylchlorosilane, and octadecyldimethyl-(3-(trimethoxysilyl)-propyl)ammonium chloride, water, and an alkoxide compound selected from the group consisting of $Si(OC_2H_5)_4$, $B(OC_2H_5)_3$, $P(OC_2H_5)_3$, $P(OCH_3)_3$, $Al(O-iso-C_3H_7)_3$, $Ti(O-iso-C_3H_7)_4$, $Zr(O-t-C_4H_9)_4$, $Zr(O-n-C_4H_9)_4$, $Ca(OC_2H_5)_2$, $Fe(OC_2H_5)_3$, $V(O-iso-C_3H_7)_4$, $Sn(O-t-C_4H_9)_4$, $Li(OC_2H_5)$, and $Be(OC_2H_5)_3$, so as to cause the hydrolysises of said alkoxide compound and the silane coupling agent, said acid catalyst being selected from the group consisting of hydrochloric acid, sulfuric acid, nitric acid, tartaric acid, phthalic acid, maleic acid, dodecysuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride; and adding an organic monomer to the reaction mixture, said organic monomer being selected from the group consisting of acrylic acid, methacrylic acid, dimethylformamide, acrylonitrile, styrene, methyl acrylate, ethyl acrylate, methyl methacrylate, and ethyl methacrylate, adding a base catalyst to said reaction mixture, and immediately thereafter irradiating the reaction mixture with ultraviolet light or an electron beam, so that a polycondensation and a polymerization occur to form said conjugated polymer, said base catalyst being a tertiary amine that is substantially insoluble in water and soluble in organic solvents, said polycondensation occurring with the hydrolysis product of said alkoxide compound and the hydrolysis product of said silane coupling agent, and said polymerization occurring between said organic monomers and the hydrolysis product of said silane coupling agent.

10. A method according to claim 9, wherein said tertiary amine is at least one selected from the group consisting of N,N-dimethylbenzylamine, tributylamine, tri-n-propylamine, tripentylamine, tripropargylamine, N,N,N-trimethylethylenediamine, and tri-n-hexylamine.

11. A method according to claim 9, wherein said silane coupling agent is added in the proportion of 1 to 300 parts by weight for every 100 parts by weight of said alkoxide compound.

12. A method according to claim 9, wherein said organic monomer is added in the proportion of 3 to 300 parts by weight for every 100 parts by weight of said alkoxide compound.

13. A method according to claim 9, wherein said acid and base catalysts are added in amounts of 0.01 mol or more for every mole of said alkoxide compound, respectively.

14. A method according to claim 9, wherein water for the hydrolysis is added in the proportion of 1 to 30 mol for every mole of said alkoxide compound.

15. A method for the production of a composite substance comprising the further step of firing the conjugated polymer obtained in claim 4 at a temperature in the range of 300° C. to 1300° C.

16. A method according to claim 15, wherein said tertiary amine is at least one selected from the group consisting of N,N-dimethylbenzylamine, tributylamine, tri-n-propylamine, tripentylamine, tripropargylamine, N,N,N-trimethylethylenediamine, and tri-n-hexylamine.

17. A method according to claim 15, wherein said silane coupling agent is added in the proportion of 1 to 300 parts by weight for every 100 parts by weight of said alkoxide compound.

18. A method according to claim 15, wherein said acid and base catalysts are added in amounts of 0.01 mol or more for every mole of said alkoxide compound, respectively.

19. A method according to claim 15, wherein water for the hydrolysis is added in the proportion of 1 to 30 mol for every mole of said alkoxide compound.

20. A method for the production of a composite substance comprising the further step of firing the conjugated polymer obtained in claim 9 at a temperature range of 300° C. to 1300° C.

21. A method according to claim 20, wherein said tertiary amine is at least one selected from the group consisting of N,N-dimethylbenzylamine, tributylamine, tri-n-propylamine, tripentylamine, tripropargylamine, N,N,N-trimethylethylenediamine, and tri-n-hexylamine.

22. A method according to claim 20, wherein said silane coupling agent is added in the proportion of 1 to 300 parts by weight for every 100 parts by weight of said alkoxide compound.

23. A method according to claim 20, wherein said organic monomer is added in the proportion of 3 to 300 parts by weight for every 100 parts by weight of said alkoxide compound.

24. A method according to claim 20, wherein said acid and base catalysts are added in amounts of 0.01 mol or more for every mole of said alkoxide compound, respectively.

25. A method according to claim 20, wherein water for the hydrolysis is added in the proportion of 1 to 30 mol for every mole of said alkoxide compound.

26. A composite substance comprising a conjugated polymer, obtained from the method comprising the steps of:

adding an acid catalyst to a reaction mixture containing a silane coupling agent selected from the group consisting of (gamma-glycidoxypropyl)trimethoxysilane, (gamma-glycidoxypropyl)methyldiethoxysilane, beta-(3,4-epoxycyclohexyl)ethyltrimethoxysilane, vinyltrimethoxysilane, vinyltrichlorosilane, vinyltris(beta-methoxyethoxy)silane, vinyltriacetoxysilane, (gamma-methacryloxypropyl)trimethoxysilane, N-beta-(N-vinylbenzylaminoethyl)-gamma-aminopropyltrimethoxysilane, hydrochloride, gamma-aminopropyltriethoxysilane, N-phenyl-gamma-aminopropyltrimethoxysilane, gamma-(2-aminoethyl)aminopropyltrimethoxysilane, gamma-(2-aminoethyl)aminopropylmethyldimethoxysilane, gamma-mercaptopropyltrimethoxysilane, gamma-mercaptopropylmethyldimethoxysilane, methyltrimethoxysilane, methyltriethoxysilane, hexamethyldisilazane, gamma-anilinopropyltrimethoxysilane, gamma-chloropropylmethyldimethoxysilane, methyltrichlorosilane, dimethyldichlorosilane, trimethylchlorosilane, and octadecyldimethyl-(3-(trimethoxysilyl)propyl)ammonium chloride, water, and an alkoxide compound selected from the group consisting of $Si(OC_2H_5)_4$, $B(OC_2H_5)_3$, $P(OC_2H_5)_3$, $P(OCH_3)_3$, $Al(O-iso-C_3H_7)_3$, $Ti(O-iso-C_3H_7)_4$, $Zr(O-t-C_4H_9)_4$, $Zr(O-n-C_4H_9)_4$, $Ca(OC_2H_5)_2$, $Fe(OC_2H_5)_3$, $V(O-iso-C_3H_7)_4$, $Sn(O-t-C_4H_9)_4$, $Li(OC_2H_5)$, and $Be(OC_2H_5)_3$, so as to cause the hydrolysis of the alkoxide compound and the silane coupling agent, said acid catalyst being selected from the group consisting of hydrochloric acid, sulfuric acid, nitric acid, tartaric acid, phthalic acid, maleic acid, dodecylsuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride, adding a base catalyst to the reaction mixture and irradiating the reaction mixture with ultraviolet light or an electron beam after the addition of said base catalyst thereto, so as to cause the polycondensation of the hydrolysis product of said alkoxide compound, and the hydrolysis product of the silane coupling agent, to form said conjugated polymer, said base catalyst being a tertiary amine that is substantially insoluble in water and soluble in organic solvents.

27. A method according to claim 4, wherein said reaction mixture further comprises diacetyl as a light-sensitizer when the reaction mixture is irradiated with ultraviolet light.

28. A method according to claim 9, wherein said reaction mixture further comprises diacetyl as a light-sensitizer when the reaction mixture is irradiated with ultraviolet light.

* * * * *